United States Patent
Spigelmyer

(10) Patent No.: US 10,610,895 B2
(45) Date of Patent: Apr. 7, 2020

(54) MONOLITHIC CUPS FOR ULTRASOUND TRANSDUCERS AND METHODS OF MAKING ULTRASOUND TRANSDUCERS

(71) Applicant: Transducer Works LLC, Centre Hall, PA (US)

(72) Inventor: Matthew Todd Spigelmyer, Spring Mills, PA (US)

(73) Assignee: TRANSDUCERWORKS, LLC, Centre Hall, PA (US)

(*) Notice: Subject to any disclaimer, the term of this patent is extended or adjusted under 35 U.S.C. 154(b) by 346 days.

(21) Appl. No.: 14/522,111

(22) Filed: Oct. 23, 2014

(65) Prior Publication Data
US 2016/0118571 A1    Apr. 28, 2016

(51) Int. Cl.
*A61B 8/00* (2006.01)
*B06B 1/06* (2006.01)

(52) U.S. Cl.
CPC .......... *B06B 1/067* (2013.01); *A61B 8/4483* (2013.01)

(58) Field of Classification Search
None
See application file for complete search history.

(56) References Cited

U.S. PATENT DOCUMENTS

| | | | | |
|---|---|---|---|---|
| 5,541,468 A | * | 7/1996 | Frey | A61B 8/546 310/327 |
| 6,406,433 B1 | * | 6/2002 | Mamayek | A61B 8/12 29/25.35 |
| 2006/0100522 A1 | * | 5/2006 | Yuan | A61B 8/12 600/466 |
| 2007/0164632 A1 | * | 7/2007 | Adachi | A61B 8/4483 310/311 |
| 2009/0234233 A1 | * | 9/2009 | Nagano | A61B 8/12 600/462 |
| 2011/0264012 A1 | * | 10/2011 | Lautzenhiser | A61N 7/00 601/2 |
| 2013/0090561 A1 | * | 4/2013 | Kusukame | A61B 8/14 600/443 |
| 2014/0163382 A1 | * | 6/2014 | Gubbini | A61B 8/4281 600/461 |

* cited by examiner

*Primary Examiner* — Jonathan Cwern
(74) *Attorney, Agent, or Firm* — J. Clinton Wimbish; Nexsen Pruet, PLLC

(57) ABSTRACT

In one aspect, ultrasound transducers are described herein comprising monolithic caps having low acoustic impedance. Such transducers can be safer to use and/or simpler to manufacture. A transducer described herein, in some embodiments, a casing, a transducer element assembly disposed in the casing, an impedance matching layer assembly positioned over the transducer element assembly, and a monolithic thermoplastic cup enclosing the inner impedance matching layer assembly, the monolithic thermoplastic cup comprising side walls extending over side walls of the casing and an impedance matching bottom wall having an acoustic impedance of 1.5 MRayls to 4.0 MRayls.

17 Claims, 3 Drawing Sheets

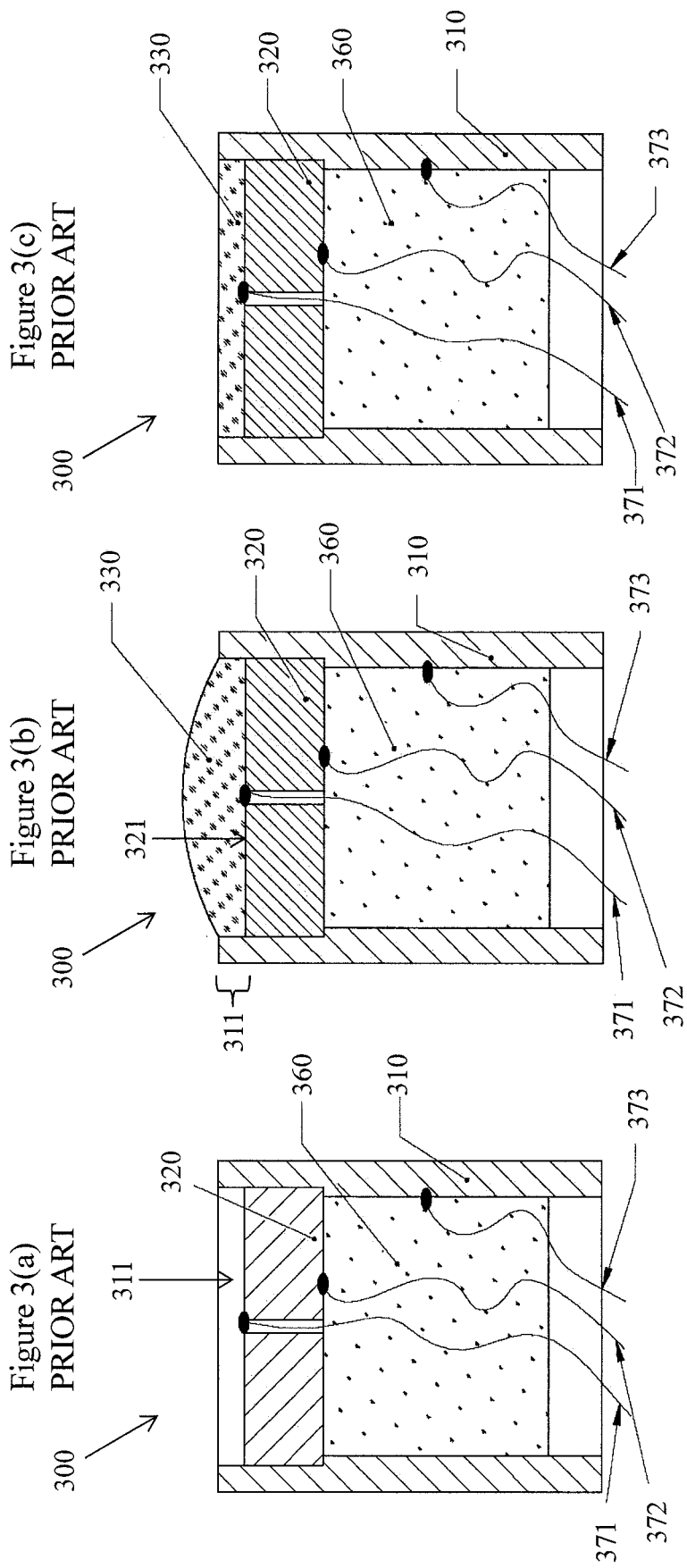

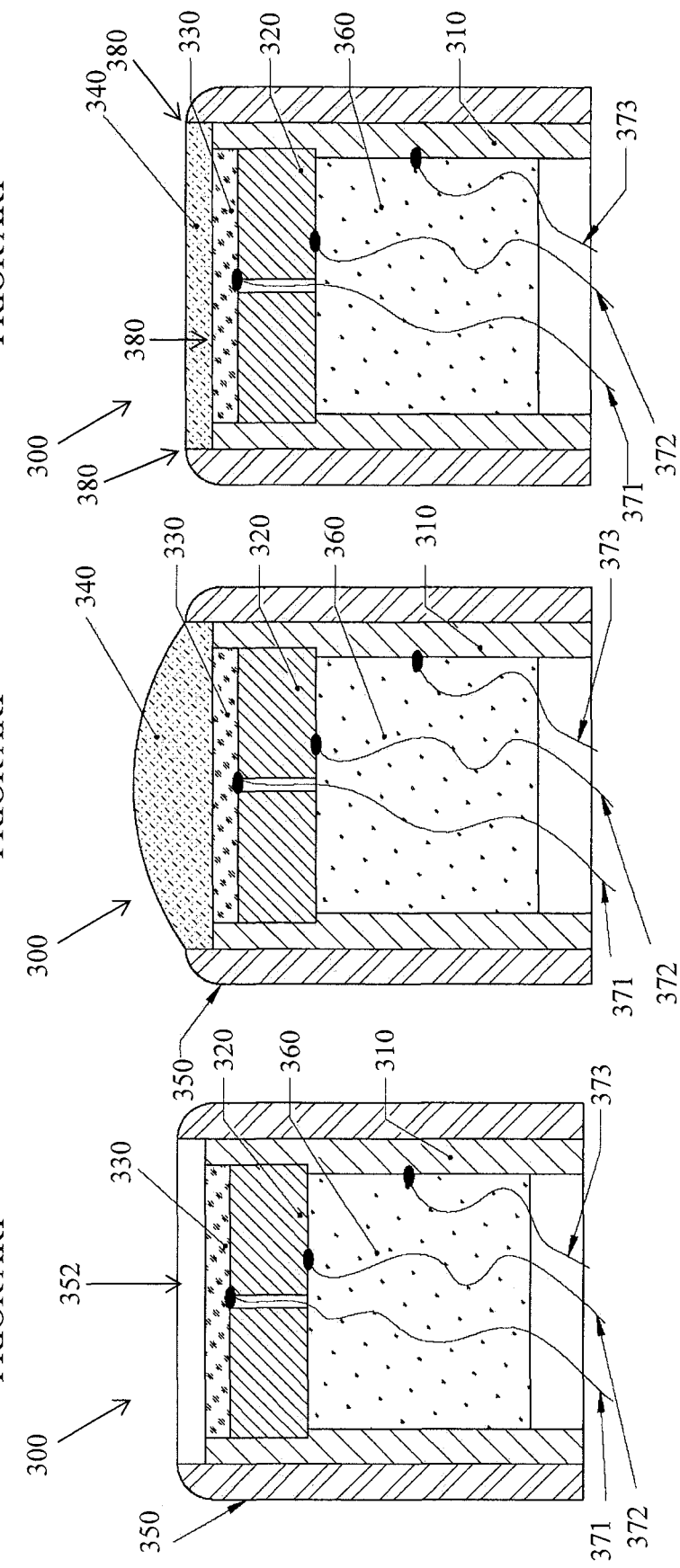

US 10,610,895 B2

MONOLITHIC CUPS FOR ULTRASOUND TRANSDUCERS AND METHODS OF MAKING ULTRASOUND TRANSDUCERS

FIELD

The present invention relates to ultrasound transducer constructions and, in particular, to transducer constructions employing a monolithic thermoplastic cup.

BACKGROUND

Typical ultrasound transducers use piezoelectric ceramic elements coupled to acoustic impedance matching layers. The impedance matching layers can improve transmission of ultrasound energy into a medium, thereby improving the efficiency of the transducer. Previously, matching layers have been fabricated directly on the piezoelectric ceramic elements, followed by machining or other altering of the matching layers to obtain a desired matching layer thickness. Further, to obtain a stack of matching layers, some prior methods repeat the foregoing process iteratively with different matching layer materials.

Unfortunately, such a fabrication method can be labor intensive and/or expensive. In addition, air entrapped in one or more matching layers formed in this manner can result in undesired electrical contact between one or more components of the transducer and a medium in contact with the transducer, such as the body of a patient. Moreover, some materials used to form impedance matching layers are mechanically weak and thus prone to damage over time. Further, prior methods of making a transducer result in the formation of joints, seams or interfaces between transducer components. Such joints or seams can exhibit debonding or delamination over time, resulting in degradation of device performance and/or electrical contact between the transducer and a medium in physical contact with the transducer. Therefore, improved ultrasound transducers and methods of making ultrasound transducers are needed.

SUMMARY

In one aspect, an ultrasound transducer is described herein employing a monolithic thermoplastic cup or enclosure, wherein a wall of the cup provides an exterior patient side impedance matching layer. The monolithic construction of the cup reduces the number of joints or seams found in the working portion of traditional ultrasound transducers, thereby providing a more robust design and efficient assembly. Further, the thermoplastic construction of the cup enhances wear resistance and provides desirable isolation of transducer electrical components. An ultrasound transducer described herein comprises a casing and a transducer element assembly disposed in the casing. An inner impedance matching layer assembly is positioned over the transducer element assembly, and a monolithic thermoplastic cup encloses the inner impedance matching layer assembly. The monolithic thermoplastic cup comprises side walls extending over side walls of the casing and an impedance matching bottom wall having an acoustic impedance of 1.5 MRayls to 4.0 MRayls. The bottom wall can have a thickness of ¼λ, wherein λ is a wavelength of the ultrasound beam generated by the transducer element assembly.

In another aspect, methods of making an ultrasound transducer are described herein which, in some embodiments, can be simpler and/or less labor intensive than prior methods. A method of making an ultrasound transducer comprises positioning a transducer element assembly in a casing and forming an inner impedance matching layer assembly over the transducer element assembly. The inner impedance matching layer assembly is subsequently enclosed with a monolithic thermoplastic cup comprising side walls and an impedance matching bottom wall, the side walls extending over side walls of the casing and the impedance matching bottom wall having an acoustic impedance of 1.5 MRayls to 4.0 MRayls. As described herein, the bottom wall can have a thickness of ¼λ, wherein λ is a wavelength of the ultrasound beam generated by the transducer element assembly.

In a further aspect, methods of imaging tissue of a patient are described herein. A method of imaging comprises providing an ultrasound transducer and imaging tissue of a patient with the ultrasound transducer, the ultrasound transducer comprising a casing, a transducer element assembly positioned in the casing and an impedance matching layer assembly positioned over the transducer element assembly. A monolithic thermoplastic cup encloses the inner impedance matching layer assembly, the monolithic thermoplastic cup comprising side walls extending over side walls of the casing and an impedance matching bottom wall having an acoustic impedance of 1.5 MRayls to 4.0 MRayls.

These and other embodiments are described in further detail in the detailed description which follows.

BRIEF DESCRIPTION OF THE DRAWINGS

FIGS. 3(a)-3(f) each illustrates a cross-sectional view of a step of a prior method of making an ultrasound transducer.

DETAILED DESCRIPTION

Embodiments described herein can be understood more readily by reference to the following detailed description, examples and drawings and their previous and following descriptions. Elements, apparatus and methods described herein, however, are not limited to the specific embodiments presented in the detailed description, examples and drawings. It should be recognized that these embodiments are merely illustrative of the principles of the present invention. Numerous modifications and adaptations will be readily apparent to those of skill in the art without departing from the spirit and scope of the invention.

I. Ultrasound Transducers

Figure 1:
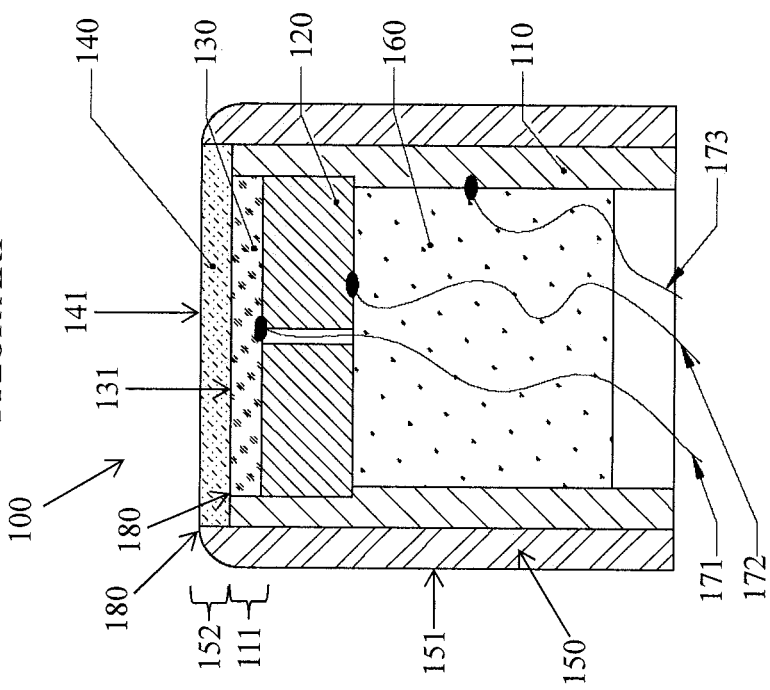
FIG. 1 illustrates a cross-sectional view of a prior ultrasound transducer.

FIG. 1 illustrates a cross-sectional view of a prior ultrasound transducer having a common structure and manufactured using a traditional method. The ultrasound transducer (100) of FIG. 1 has a generally cylindrical shape and includes a first casing (110) formed of brass. The first casing (110) serves as a housing for additional components of the transducer (100). Specifically, a piezoelectric ceramic transducer element (120) is disposed in the first casing (110), and a high impedance matching layer (130) is disposed on and positioned over the transducer element (120). The high impedance matching layer (130) is a machined layer having a substantially flat or planar top surface (131). Further, the high impedance matching layer (130) is positioned within a well or depression (111) formed or defined by the first casing (110). In addition, a low impedance matching layer (140) is disposed on and positioned over the high impedance matching layer (130) in a stacked configuration. Like the high impedance matching layer (130), the low impedance matching layer (140) is a machined layer having a substantially flat or planar top or exterior surface (141). The low impedance matching layer (140) is positioned in a well or depression (152) defined by a second casing (150) formed of a plastic material. The second casing (150) surrounds the first casing (110).

In this manner, the second casing (150) can provide an electrically insulating surface (151) for gripping or handling of the transducer by a user. The transducer (100) further comprises a backing material (160) positioned in the first casing (110) and coupled to the piezoelectric ceramic transducer element (120). The transducer (100) also includes electrical wires and contacts (171, 172, 173) disposed within the first casing (110). Specifically, the transducer (100) comprises a negative wire (171), a positive wire (172), and a shield wire (173). In addition, as illustrated in FIG. 1, the transducer (100) includes seams or joints (180) between various components of the transducer (100). As described herein, the seams or joints (180) can introduce failure modes in the transducer (100). Specifically, the seams or joints (180) can result in electrical contact between the exterior surface (141) and a medium, such as a patient, in physical contact with the exterior surface (141). In this manner, the transducer (100) can provide undesired or unintended electrical shocks to a medium or a patient.

However, an ultrasound transducer described herein employs a monolithic thermoplastic cup or enclosure, wherein a wall of the cup provides an exterior patient side impedance matching layer. In being monolithic, the cup is formed of a single piece of thermoplastic material. For example, the monolithic thermoplastic cup can be formed by a molding operation, such as injection molding. Alternatively, the cup can be machined from a monolithic piece of thermoplastic material. Any thermoplastic material meeting the low acoustic impedance requirements set forth herein can be used for the monolithic cup. In some embodiments, the thermoplastic is selected from the group consisting of polyethylene, polymethylpentene (TPX), polyetherimide and ionomer such as SURLYN®.

In being monolithic, the thermoplastic cup presents a seamless or jointless exterior working surface, thereby reducing the number of failure modes for performance degradation and/or undesired electrical contact between transducer components and a medium in contact with the transducer.

Figure 2:
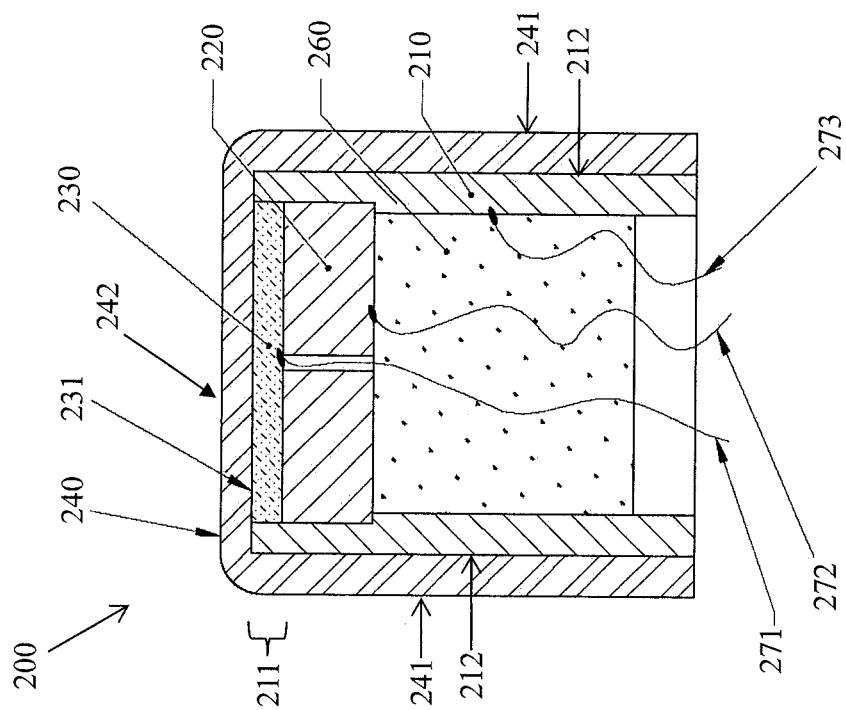
FIG. 2 illustrates a cross-sectional view of an ultrasound transducer according to one embodiment described herein.

FIG. 2 illustrates a cross-sectional view of an ultrasound transducer according to one embodiment described herein. The ultrasound transducer (200) of FIG. 2 has a cylindrical shape and includes a casing (210). The casing (210) can be formed of any suitable material, such as brass or other alloy. The casing (210) serves as a housing for additional components of the transducer (200). Specifically, a transducer element assembly (220) is positioned in the casing (210). In addition, an inner impedance matching layer assembly (230) is disposed on and positioned over the array of transducer element assembly (220). The inner impedance matching layer assembly (230) can be formed of one or more layers of material having high acoustic impedance. The inner impedance matching layer assembly (230) can be machined to have a substantially flat or planar top surface (231). Further, the inner impedance matching layer assembly (230) is positioned within a well or depression (211) formed or defined by the casing (210).

However, unlike the ultrasound transducer (100) of FIG. 1, the ultrasound transducer (200) of FIG. 2 does not necessarily comprise a low impedance matching layer directly formed on the inner impedance matching layer assembly (230). Instead, the ultrasound transducer (200) of FIG. 2 comprises a monolithic thermoplastic cup (240) enclosing the inner impedance matching layer assembly (230). The monolithic thermoplastic cup (240) comprises side walls (241) extending over side walls (212) of the casing (210). In some embodiments, an adhesive is positioned between the casing side walls (212) and cup side walls (241) to secure the thermoplastic cup (240). The monolithic thermoplastic cup (240) also comprises a bottom wall (242) having an acoustic impedance of 1.5 MRayls to 4.0 MRayls. The bottom wall can also exhibit a thickness of ¼λ, wherein λ is a wavelength of the ultrasound beam generated by the array of transducer elements. In the embodiment illustrated in FIG. 2, the interior surface of the bottom wall (242) contacts the inner impedance matching layer assembly (230). The exterior surface of the bottom wall (242) serves as a patient contact surface.

An ultrasound beam generated by the transducer element assembly (220) can have any ultrasound frequency not inconsistent with the objectives of the present disclosure. The ultrasound beam, for example, can have a frequency suitable for imaging human or animal tissue. In other embodiments, the ultrasound beam can have a frequency suitable to measure blood flow via Doppler Effect principles. Moreover, the ultrasound beam can have a frequency suitable for administering a therapeutic effect, such as accelerating the delivery of one or more pharmaceutical agents to the tissue.

Moreover, as well as replacing the function of the low impedance matching layer (140) of the transducer (100) of FIG. 1, the monolithic thermoplastic cup (240) of the transducer (200) can also simultaneously replace the function of the second casing (150). Side walls (241) of the monolithic thermoplastic cup (240), for example, can provide an electrically insulating surface (241) for gripping or handling by a user of the transducer. In addition, as illustrated in FIG. 2, the transducer (200) further comprises a backing material (260) disposed in the casing (210). The backing material (260) is coupled to the transducer element assembly (220) and is disposed between the array (220) and the casing (210). The transducer (200) also includes electrical wires and contacts (271, 272, 273) disposed within the casing (210). Specifically, the transducer (200) comprises a negative wire (271), a positive wire (272), and a shield wire (273).

Turning now to additional specific components, an ultrasound transducer described herein comprises a transducer element assembly. The transducer element assembly, in some embodiments, is a single transducer element. Alternatively, the transducer element assembly can comprise a plurality of transducer elements, including an array of transducer elements. In some embodiments, transducer elements are formed of a piezoelectric material. Suitable piezoelectric materials include but are not limited to a monolithic piezoelectric ceramic material or a composite material, such as a ceramic-epoxy composite. In some cases, for example, the piezoelectric material of elements of the array is a lead zirconium titanate. Other materials may also be used. Further, in some instances, the piezoelectric material can have a curved shape such as a spherical shape to provide acoustic focusing.

In some embodiments, an array of transducer elements comprises a piezoelectric material separated or divided into N transducer elements in the axial direction to provide an N×1 array. N, in some embodiments, is 64 or a multiple of 64. In some cases, N is 128, 192, 256, 320, 384, 448 or 512.

Moreover, in some instances, the array of transducer elements comprises a piezoelectric material separated or divided into N transducer groups in the axial direction and M transducer elements in the longitudinal direction transverse to the axial direction to provide an N×M array. In some embodiments, N of an N×M array is 64 or a multiple of 64, including 128, 192, 256, 320, 384, 448 or 512. In some cases, N of an N×M array is greater than 512.

Piezoelectric transducer elements of an array described herein, in some instances, each comprise individual positive and ground electrodes. The positive and ground electrodes can be positioned on opposing surfaces of the piezoelectric transducer element, such as top and bottom surfaces of the element. Top and bottom surfaces of a piezoelectric transducer element can be defined relative to the medium to be imaged with the top surface of the piezoelectric element proximate the medium and the bottom surface distal to the medium.

II. Methods of Making an Ultrasound Transducer Assembly

In another aspect, methods of making an ultrasound transducer are described herein. A method of making an ultrasound transducer comprises positioning a transducer element assembly in a casing and forming an inner impedance matching layer assembly over the transducer element assembly. The inner impedance matching layer assembly is enclosed with a monolithic thermoplastic cup comprising side walls and an impedance matching bottom wall, the side walls extending over side walls of the casing and the impedance matching bottom wall having an acoustic impedance of 1.5 MRayls to 4.0 MRayls. The monolithic thermoplastic cup can have any properties and/or construction described in Section I hereinabove. The bottom wall, for example, can have thickness of ¼λ, wherein λ is a wavelength of the ultrasound beam generated by the transducer element assembly. Further, the resulting ultrasound transducer assembly can have any construction and/or properties described in Section I above.

A method described herein may also comprise disposing a backing material in the casing and coupling the backing material to the array of transducer elements. The backing material can be coupled to the array of transducer elements in any manner not inconsistent with the objectives of the present disclosure. For example, in some cases, the backing material is coupled to the array of transducer elements using an adhesive.

Methods of making an ultrasound transducer described herein can be contrasted with some prior methods. FIGS. 3(a)-3(f) illustrate cross-sectional views of a prior method of making an ultrasound transducer (300). In a first step, as illustrated in FIG. 3(a), a piezoelectric ceramic transducer element (320), backing material (360) and electrical wires and contacts (371, 372, and 373) are positioned in a brass first casing (310). Next, as illustrated in FIG. 3(b), a high impedance matching layer (330) is cast directly onto the top surface (321) of the piezoelectric ceramic transducer element (320). Specifically, the material used to farm the high impedance matching layer (330) is cast into a well or depression (311) formed or defined by the first casing (310) and the top surface (321) of the piezoelectric ceramic transducer element (320). Thus, the walls of the first casing (310) "dam" or contain the high impedance material. The high impedance matching layer (330) is then machined to the desired thickness, as illustrated in FIG. 3(c).

The foregoing process is then repeated with a low impedance material to form a low impedance matching layer (340), as illustrated in FIGS. 3(d)-3(f). Specifically, as illustrated in FIG. 3(d), a second casing (350), in this instance formed of a plastic, is disposed over the first casing (310) to substantially surround the first casing (310). Then, the material used to form the low impedance matching layer (340) is cast into a well or depression (352) formed or defined by the second casing (350). Thus, the walls of the second casing (350) "dam" or contain the low impedance material, as illustrated in FIG. 3(e). The low impedance matching layer (340) is then machined to the desired thickness, as illustrated in FIG. 3(f), to provide the completed transducer (300). As described herein, the transducer (300) comprises joints or seams (380) as a result of the foregoing manufacturing process. These joints or seams can provide failure modes for the transducer, possibly resulting in electrical shock of a patient or user of the transducer (300).

In contrast to the method of FIGS. 3(a)-3(f), a method of making an ultrasound transducer according to an embodiment described herein can be carried out by positioning the monolithic thermoplastic cup over the partially formed transducer (300) depicted in FIG. 3(c), thereby providing an ultrasound transducer having a structure similar to ultrasound transducer (200) of FIG. 2. Use of the monolithic thermoplastic cup realizes fabrication efficiencies and provides a transducer of more robust construction.

III. Methods of Imaging

In a further aspect, methods of imaging tissue of a patient are described herein. A method of imaging comprises providing an ultrasound transducer and imaging tissue of a patient with the ultrasound transducer, the ultrasound transducer comprising a casing, a transducer element assembly positioned in the casing and an impedance matching layer assembly positioned over the array of transducer elements. A monolithic thermoplastic cup encloses the inner impedance matching layer assembly, the monolithic thermoplastic cup comprising side walls extending over side walls of the casing and an impedance matching bottom wall having an acoustic impedance of 1.5 MRayls to 4.0 MRayls. The bottom wall, in some embodiments, has thickness of ¼λ, wherein λ is a wavelength of the ultrasound beam generated by the array of transducer elements. Further, the resulting ultrasound transducer assembly can have any construction and/or properties described in Section I above.

Alternatively, an ultrasound transducer described herein can be employed to measure blood flow via Doppler Effect principles. Moreover, an ultrasound transducer described herein can be used in applications where ultrasound energy is provided to administer a therapeutic effect, such as accelerating the delivery of one or more pharmaceutical agents to the tissue.

Various embodiments of the invention have been described in fulfillment of the various objects of the invention. It should be recognized that these embodiments are merely illustrative of the principles of the present invention. Numerous modifications and adaptations thereof will be readily apparent to those skilled in the art without departing from the spirit and scope of the invention.

The invention claimed is:

1. An ultrasound transducer comprising:
a casing;
a transducer element assembly positioned in the casing;
an inner impedance matching layer assembly positioned in the casing over the transducer element assembly; and
a monolithic electrically insulating thermoplastic cup bonded to portions of the casing, wherein the monolithic electrically insulating thermoplastic cup encloses and contacts the inner impedance matching layer assembly, wherein the monolithic electrically insulating thermoplastic cup comprises side walls and an impedance matching bottom wall, the side walls extending over and contacting side walls of the casing, and the impedance matching bottom wall having an acoustic impedance of 1.5 MRayls to 4.0 MRayls.

2. The ultrasound transducer of claim 1, wherein the side walls and bottom wall of the monolithic thermoplastic cup form exterior surfaces of the ultrasound transducer.

3. The ultrasound transducer of claim 1, wherein the bottom wall has thickness of $\frac{1}{4}\lambda$, wherein $\lambda$ is a wavelength of the ultrasound beam generated by the transducer element assembly.

4. The ultrasound transducer of claim 1, wherein the bottom wall contacts the inner impedance matching layer assembly.

5. The ultrasound transducer of claim 1, wherein the inner impedance matching layer assembly comprises a plurality of inner impedance matching layers.

6. The ultrasound transducer of claim 1, wherein the transducer element assembly comprises one or more piezoelectric ceramic transducer elements.

7. The ultrasound transducer of claim 1 further comprising a backing material disposed in the casing and coupled to the transducer element assembly.

8. The ultrasound transducer of claim 1, wherein the casing is formed of an alloy.

9. A method of making an ultrasound transducer comprising:
   positioning a transducer element assembly in a casing;
   forming an inner impedance matching layer assembly over the transducer element assembly and in the casing; and
   bonding a monolithic electrically insulating thermal cup to portions of the casing, wherein the cup encloses and contacts the inner impedance matching layer assembly, the cup comprising side walls and an impedance matching bottom wall, the side walls extending over side walls of the casing and the impedance matching bottom wall having an acoustic impedance of 1.5 MRayls to 4.0 MRayls.

10. The method of claim 9, wherein the side walls and bottom wall of the monolithic thermoplastic cup form exterior surfaces of the ultrasound transducer.

11. The method of claim 9, wherein the bottom wall has thickness of $\frac{1}{4}\lambda$, wherein $\lambda$ is a wavelength of the ultrasound beam generated by the transducer element assembly.

12. The method of claim 9, wherein the bottom wall contacts the inner impedance matching layer assembly.

13. The method of claim 9, wherein the inner impedance matching layer assembly is cast over the transducer element assembly and machined.

14. A method of imaging comprising:
   providing an ultrasound transducer and imaging tissue of a patient with the ultrasound transducer, the ultrasound transducer comprising a casing, a transducer element assembly disposed in the casing, an impedance matching layer assembly positioned over the transducer element assembly and in the casing, and a monolithic electrically insulating thermoplastic cup bonded to portions of the casing, wherein the monolithic electrically insulating thermoplastic cup encloses and contacts the inner impedance matching layer assembly, the monolithic electrically insulating thermoplastic cup comprising side walls extending over side walls of the casing and an impedance matching bottom wall having an acoustic impedance of 1.5 MRayls to 4.0 MRayls.

15. The method of claim 14, wherein an exterior surface of the bottom wall contacts the patient or a coupling medium applied to the patient.

16. The method of claim 14, wherein the bottom wall has thickness of $\frac{1}{4} \lambda$, wherein $\lambda$ is a wavelength of the ultrasound beam generated by the array of transducer elements.

17. The method of claim 14, wherein the bottom wall contacts the inner impedance matching layer assembly.

* * * * *